United States Patent [19]
Cameron et al.

[11] Patent Number: 5,889,388
[45] Date of Patent: Mar. 30, 1999

[54] CIRCUITRY FOR DYNAMICALLY CONTROLLING CAPACITOR CHARGE BASED ON BATTERY CAPACITY

[75] Inventors: David B. Cameron, Seattle; Daniel J. Powers, Issaquah; Douglas H. Roberts, Bellevue, all of Wash.

[73] Assignee: Heartstream, Inc., Seattle, Wash.

[21] Appl. No.: 662

[22] Filed: Dec. 30, 1997

Related U.S. Application Data

[62] Division of Ser. No. 659,503, Jun. 6, 1996, Pat. No. 5,773,961.

[51] Int. Cl.$^6$ .......................... H01M 10/44; H01M 10/46
[52] U.S. Cl. ................................................ 320/166
[58] Field of Search ..................... 320/138, 132, 320/134, 136, 143, 162, 166, 100, 139

[56] References Cited

U.S. PATENT DOCUMENTS

| | | |
|---|---|---|
| 4,207,514 | 6/1980 | Klein . |
| 4,259,639 | 3/1981 | Renirie . |
| 4,525,055 | 6/1985 | Yokoo . |
| 4,590,943 | 5/1986 | Paull et al. . |
| 4,693,119 | 9/1987 | Johnson . |
| 4,725,784 | 2/1988 | Peled et al. . |
| 5,065,084 | 11/1991 | Oogita . |
| 5,130,659 | 7/1992 | Sloan . |
| 5,162,741 | 11/1992 | Bates . |
| 5,250,905 | 10/1993 | Kuo et al. . |
| 5,285,779 | 2/1994 | Cameron et al. . |
| 5,483,165 | 1/1996 | Cameron . |
| 5,489,293 | 2/1996 | Pless et al. . |
| 5,554,174 | 9/1996 | Causey, III . |
| 5,583,416 | 12/1996 | Klang . |
| 5,591,213 | 1/1997 | Morgan . |

OTHER PUBLICATIONS

Weaver et al. "Use of Automatic External Defibrillator in the Management of Out–of–Hospital Cardiac Arrest" *N.E. J. Med.* 319:661 (1988).

*Primary Examiner*—Edward H. Tso

[57] ABSTRACT

A method and apparatus for indicating a low battery condition and for dynamically controlling the load on a battery in order to optimize battery usage. A dynamic load controller for a battery includes detection circuitry for measuring at least one condition related to battery capacity, and power control circuitry for adjusting a power load on the battery based upon the condition. The dynamic load controller may be employed to control the power load on a battery that powers an electrotherapy device, such as a defibrillator. The battery condition may include the slope of a capacity curve, which may be the product of the battery voltage and the power delivered from the battery as a function of the delivered power. Based upon this condition, the power control circuitry adjusts the power load to optimize power delivery from the battery. The controller includes circuitry for indicating a low battery condition if battery voltage falls below a battery voltage threshold and the power load falls below a power threshold, or if the optimum power falls below a power threshold. The controller also includes circuitry for indicating a replace battery condition if battery voltage falls below a battery voltage threshold and the power load falls below a minimum power threshold, or if the optimum power falls below a minimum power threshold.

4 Claims, 9 Drawing Sheets

CIRCUITRY FOR DYNAMICALLY CONTROLLING CAPACITOR CHARGE BASED ON BATTERY CAPACITY

RELATED APPLICATIONS

This application is a divisional of application Ser. No. 08/659,503, filed Jun. 6, 1996, now U.S. Pat. No. 5,773,961.

FIELD OF THE INVENTION

The present invention relates to battery load controllers and battery capacity monitors generally and, in particular, to battery load controllers and battery capacity monitors for battery-operated electrotherapy devices and other battery-operated devices.

DESCRIPTION OF THE RELATED ART

When using a battery-operated device, it is often important to know when the useful life of the battery is about to end. For example, failure to indicate a low battery condition of a battery-operated computer could result in data loss if the remaining power is insufficient to save the information and exit the application. As another example, knowledge of the remaining battery capacity of a battery-operated medical device could be crucial in a medical emergency.

Electrotherapy devices are used to provide electric shocks to treat patients for a variety of heart arrhythmias. For example, external defibrillators provide relatively high-level shocks to a patient, usually through electrodes attached to the patient's torso, to convert ventricular fibrillation to a normal sinus rhythm. Similarly, external cardioverters can be used to provide shocks to convert atrial fibrillation to a more normal heart rhythm. Many electrotherapy devices are powered by batteries.

Prior art electrotherapy devices provide an indication of a low battery condition and a depleted battery condition. Stopping an electrotherapy treatment to replace a battery can have a detrimental effect on the patient being treated. None of the prior art electrotherapy devices, however, provides sufficient warning of an impending battery failure to allow an accurately predetermined minimum level or period of continued treatment before battery failure. For example, while a low battery warning on a prior art external defibrillator can mean that the battery has sufficient remaining capacity to provide one more treatment to a patient, it can also mean that the battery is so far depleted that no effective treatment is possible. The actual amount of battery capacity remaining when prior art devices indicate a low battery condition can vary with the ambient temperature, battery manufacturing variances, battery discharge history, battery recharge history, etc.

In addition, because batteries can be relatively large and heavy components of battery-operated devices (such as electrotherapy devices), it is important to use as much of the available battery capacity as possible before replacing the battery. It is also important to be able to control the battery's power delivery so that the device can be operated at an optimal level.

Batteries are rated according to a number of electrical characteristics, including voltage, capacity and acceptable current load. Within an acceptable temperature range and under acceptable load conditions, the battery is able to maintain its rated voltage. However, when heavily loaded, a battery can suffer a large drop in output voltage. The load at which this drop occurs relates to the remaining capacity of the battery.

These observations can be explained, in part, by reference to a simplified model of a battery. A battery system can be represented by a battery voltage source connected in series to an internal battery impedance that, in turn, is connected in series to a load impedance. Thus, the internal impedance in series with the load impedance acts as a voltage divider. Within limits, power to the load may be increased by decreasing the load impedance. As a result, the voltage drop across the load decreases while the voltage drop across the internal battery impedance increases. When battery capacity is low, internal battery impedance increases, thereby achieving a decrease in the voltage drop across the load. Under heavy loading, battery voltage decreases dramatically due to these and other electrochemical effects. In a more realistic system with a load that demands constant power, the battery current increases drastically as battery voltage drops to maintain constant power delivery to the load. Under sufficiently high loading conditions, this high current drain will cause a runaway condition in which current continues to rise, voltage continues to drop, and eventually power delivered to the load falls to zero.

To avoid this condition, most battery-operated systems simply maintain battery loading at a predetermined amount below a maximum acceptable power level. Typically, the battery is conservatively loaded so that a large, yet indeterminate amount of capacity remains before a low battery condition is indicated. By avoiding maximum drainage before indicating a low battery, such a system prevents battery shutdown as capacity diminishes. However, it is desirable to measure battery capacity more accurately so that the low battery indication occurs closer to actual battery depletion, and so that the remaining capacity can be estimated with greater certainty. Further, in some systems, it is desirable to deliver maximum power consistently to the load. For example, in a cardiac defibrillator, the power employed to charge an energy storage capacitor determines the speed with which the capacitor can be charged. This factor is thus especially important in life-saving situations as it affects charge time. Moreover, because the power load is typically fixed in such electrotherapeutic devices, the battery may approach shutdown as its capacity diminishes even though the battery may still store enough energy to provide effective electrotherapeutic treatment at lower power levels.

U.S. Pat. No. 5,483,165, issued to Cameron et al., and assigned to the assignee of the present invention (the disclosure of which is incorporated herein by reference) describes a battery system that can be used to provide an early indication of battery failure through the use of a sense cell in addition to the main battery. The '165 patent suggests that the sense cell can be related to the main battery such that when a sense cell parameter reaches a certain value the main battery has a predetermined remaining capacity. The '165 patent does not disclose, however, specific sense cell/main battery relationships for particular applications, nor does it address the issue of battery power control for the purpose of optimizing battery usage.

What is needed, therefore, is an instrument power system that has a battery load controller and/or a battery capacity monitor that provides an indication of a low battery condition early enough to be able to continue operating a battery-operated device at an optimal level for an effective period of time without calling for the replacement of the battery before the battery has been actually depleted.

SUMMARY OF THE INVENTION

To accomplish these and other objectives, the present invention provides a method and apparatus for indicating a low battery condition and for dynamically controlling the load on a battery in order to optimize battery usage. A dynamic load controller for a battery includes detection circuitry for measuring at least one condition related to battery capacity, and power control circuitry for adjusting a power load on the battery based upon the condition. The dynamic load controller may be employed to control the power load on a battery that powers an electrotherapy device, such as a defibrillator.

The battery condition may include the slope of a capacity curve, which may be the product of the battery voltage and the power delivered from the battery as a function of the delivered power. Based upon this condition, the power control circuitry adjusts the power load to optimize power delivery from the battery.

The controller includes circuitry for indicating a low battery condition if battery voltage falls below a battery voltage threshold and the power load falls below a power threshold, or if the optimum power falls below a power threshold. The controller also includes circuitry for indicating a replace battery condition if battery voltage falls below a battery voltage threshold and the power load falls below a minimum power threshold, or if the optimum power falls below a minimum power threshold. In a battery system having a battery that includes a main stack for powering a main load and a sense cell for powering the main load and a dummy load, the controller may be employed to disable the dummy load based upon a battery condition. In this case, the optimization circuitry optimizes power delivery to the main load at an optimum power. The battery condition that triggers the disabling of the dummy load may be the optimum power falling below a power threshold, the battery voltage falling below a battery voltage threshold when power delivery to the main load falls below a power threshold, or the sense cell voltage falling below a sense cell voltage threshold when power delivery to the main load falls below a power threshold.

In this configuration, the controller may also include circuitry for indicating a low battery condition if the optimum power falls below a power threshold, the battery voltage falls below a battery voltage threshold when power delivery to the main load falls below a power threshold, or the sense cell voltage falls below a sense cell voltage threshold when power delivery to the main load falls below a power threshold. Further, the controller may include circuitry for indicating a replace battery condition if the optimum power falls below a minimum power threshold, the battery voltage falls below a battery voltage threshold when power delivery to the main load falls below a minimum power threshold, or the sense cell voltage falls below a sense cell voltage threshold when power delivery to the main load falls below a minimum power threshold.

Initially, the optimization circuitry optimizes power delivery to the main load at an optimum power level by measuring characteristics of the sense cell, and then optimizes power delivery to the main load by measuring characteristics of the main stack if the sense cell reaches a low capacity condition. This low capacity condition may occur when the sense cell voltage falls below a sense cell voltage threshold and power delivery to the main load falls below a power threshold, or when the optimum power level obtained by measuring sense cell characteristics falls below the power threshold.

In an electrotherapy device powered by a battery, the dynamic load controller may be used to provide a battery capacity indication by operating the electrotherapy device to treat a patient, monitoring a battery parameter during the operating step, and providing a low battery capacity indication based on a value of the battery parameter. The indication is provided while the electrotherapy device can provide at least three, six or nine electrical shocks to the patient under various timing constraints before the battery is depleted. When the electrotherapy device is operated to treat the patient, it may be used to deliver a shock to the patient and monitor the patient's ECG.

BRIEF DESCRIPTION OF THE DRAWINGS

The objects, features and advantages of the present invention will be apparent to one skilled in the art in light of the following detailed description in which.

DETAILED DESCRIPTION OF THE INVENTION

The present invention provides a method and apparatus for providing an early indication of a low battery condition and/or for dynamically controlling the load on a battery. For purposes of explanation, specific details are set forth to provide a thorough understanding of the present invention. However, it will be understood by those skilled in the art, from reading this disclosure, that the invention may be practiced without these details. Moreover, well-known elements, devices, process steps and the like are not set forth in order to avoid obscuring the invention.

Figure 1:
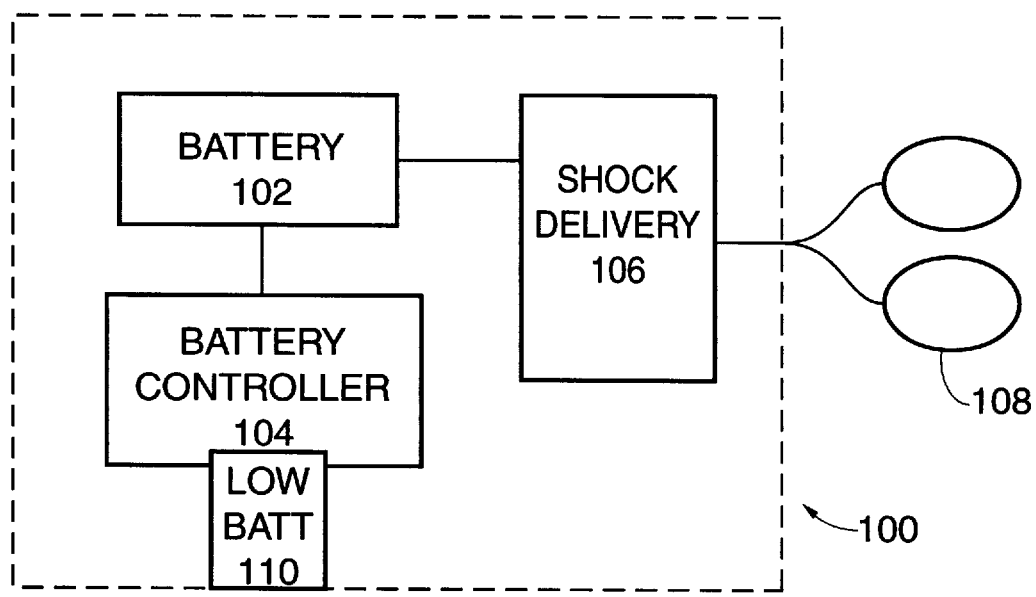
FIG. 1 is a block diagram of an electrotherapy device.

FIG. 1 is a block diagram of an electrotherapy device 100. Device 100 may be a defibrillator, a cardioverter, or any other electrotherapy device. The major components of device 100 are a battery 102, a battery capacity monitor/controller 104, and a shock delivery system 106 for delivering shocks to a patient through electrodes 108. The battery capacity monitor has a low battery capacity indicator 110 (such as a warning light, a display for text or images, an annunciator, etc.) for indicating when the remaining capacity of the battery falls below a threshold level. Device 100 may also include an optional patient monitor (not shown) for monitoring a condition of the patient.

During use of device 100 to treat a patient, battery 102 provides power to shock delivery system 106, and the shock delivery system uses this power to deliver electrical shocks through electrodes 108, as is known in the art. Battery controller 104 monitors a battery parameter related to the capacity of battery 102 during the treatment operation and provides an indication through low battery capacity indicator when a value of the monitored parameter indicates that the electrotherapy device has only a minimum capacity single use remaining before the battery is depleted. Battery controller 104 also controls the load applied to battery 102 in order to optimize the use of the remaining capacity of battery 102.

The definition of "minimum capacity single use" varies from application to application. For external defibrillators, for example, the minimum capacity single use may be defined as the ability to deliver at least three shocks at a therapeutic energy level to a patient, with the shock delivery system charging time for each shock being no greater than 60 seconds, most preferably no greater than 30 seconds. Three shocks in sequence have been shown to have a large cumulative probability of terminating cardiac fibrillation. See, e.g., Weaver, W. D., et al., "Use of the Automatic External Defibrillator in the Management of Out-of-Hospital Cardiac Arrest," 319 N. Eng. J. Med. 661 (Sep. 15, 1988). In some cases, however, the patient may not defibrillate after three shocks or may experience refibrillation, thus requiring additional shock sequences. Few patients require more than three shock sequences.

Thus, in a preferred embodiment, the minimum capacity single use of an external defibrillator is the ability to delivery at least six truncated exponential biphasic waveform shocks (corresponding to two iterations of the three-shock protocol) of at least 130 Joules to a patient, with the shock delivery system shock to shock cycle time being no greater than 60 seconds (and most preferably no greater than 30 seconds), at a temperature of 0° C. In another preferred embodiment, the minimum capacity single use of an external defibrillator is the ability to delivery at least nine truncated exponential biphasic waveform shocks (corresponding to three iterations of the three-shock protocol) of at least 130 Joules to a patient, with the shock delivery system shock to shock cycle time being no greater than 60 seconds (and with the first six shocks preferably having a cycle time of 30 seconds or less), at a temperature of 0° C.

A preferred embodiment of the invention is described below with reference to an external defibrillator. It should be understood that the invention may also be applied to all electrotherapy devices and to other battery-operated devices as well.

Figure 2:
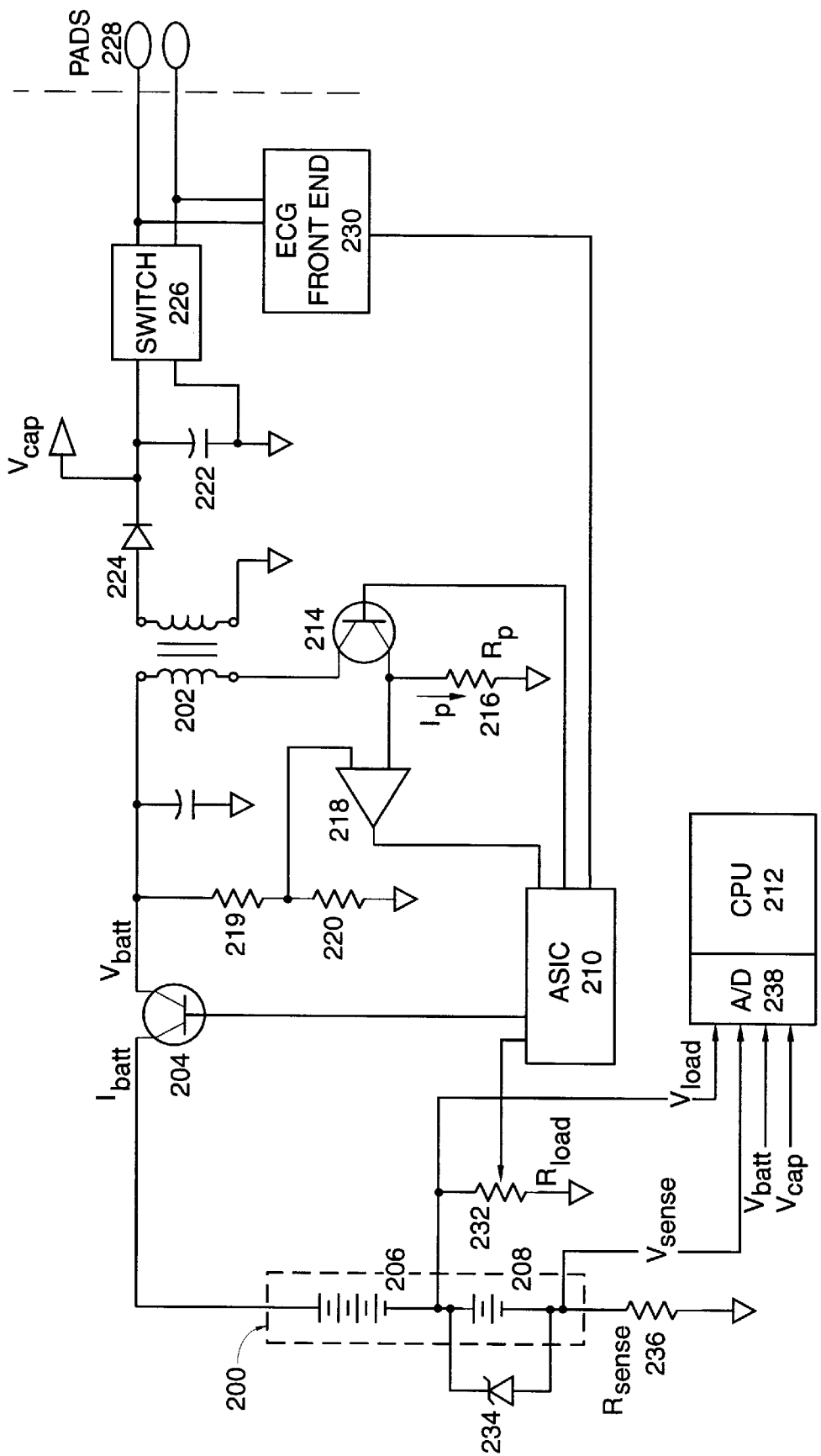
FIG. 2 illustrates a cardiac defibrillator incorporating an embodiment of a battery capacitor indicator and dynamic load controller of the present invention.

FIG. 2 illustrates a cardiac defibrillator incorporating an embodiment of a battery capacity indicator and a dynamic load controller of the present invention. Those skilled in the art will understand that the battery capacity indicator and the dynamic load controller find applicability not just in defibrillators, but in a wide variety of battery-operated systems. Referring to FIG. 2, a battery 200 is switchably coupled to a primary coil of a flyback transformer 202 through an FET power switch 204. In one embodiment, the battery 200 may be a main stack 206 and sense cell 208 arrangement like that of U.S. Pat. No. 5,483,165. Those skilled in the art will recognize that the present invention is not limited to a main stack/sense cell arrangement, but rather is generally applicable to any battery system.

The power switch 204 is controlled by an application-specific integrated circuit (ASIC) 210 through commands provided by a CPU 212. The flyback converter circuitry of the defibrillator includes the ASIC 210, an FET flyback switch 214, a flyback current-sensing resistor 216, a comparator 218, and a voltage divider comprising a first resistor 219 and a second resistor 220.

The secondary coil of the flyback transformer 202 is coupled to an energy storage capacitor 222 through a diode 224 in order to charge the energy storage capacitor 222 to the target voltage. An energy transfer switch 226 transfers the charge from the energy storage capacitor 222 to defibrillator electrodes 228 that are applied to the patient's chest. The energy transfer switch 226 is typically actuated by the user. The defibrillator also includes an ECG front end 230 coupled to the electrodes, as is well known in the art.

As described in U.S. Pat. No. 5,483,165, the ASIC 210, acting as a controller, controls a programmable dummy load 232 so that it draws an incremental current from the sense cell 208 in addition to the current passing through the main stack 206. This current is chosen to provide for a certain amount of remaining capacity in the main stack 206 after a drop in sense cell capacity indicates that the sense cell 208 has been depleted. In one preferred embodiment, for example, the incremental current is set at 25% over the current drawn from the main stack 206. Other examples are described below. A diode 234 permits the main stack 206 to be used after the sense cell has been depleted and prevents the sense cell from being electrically reversed.

A sense voltage $V_{sense}$ is measured across a sense cell current-sensing resistor $R_{sense}$ 236 and provided to an analog-to-digital converter (A/D) 238, which provides a digital representation of the voltage to the microprocessor 212. The CPU 212 calculates the current $I_{sense}$ flowing through the sense cell 208 as $$I_{sense} = \frac{V_{sense}}{R_{sense}}$$

Current that is related to (e.g., equal to, proportional to, or incrementally greater than) the current flowing through the main stack 206, $I_{batt}$, is drawn from the sense cell 208 by placing the programmable dummy load 232 $R_{load}$ between the sense cell 208 and ground. Note that $I_{batt}=I_{sense}$ when the programmable load 232 is disabled.

Figure 3:
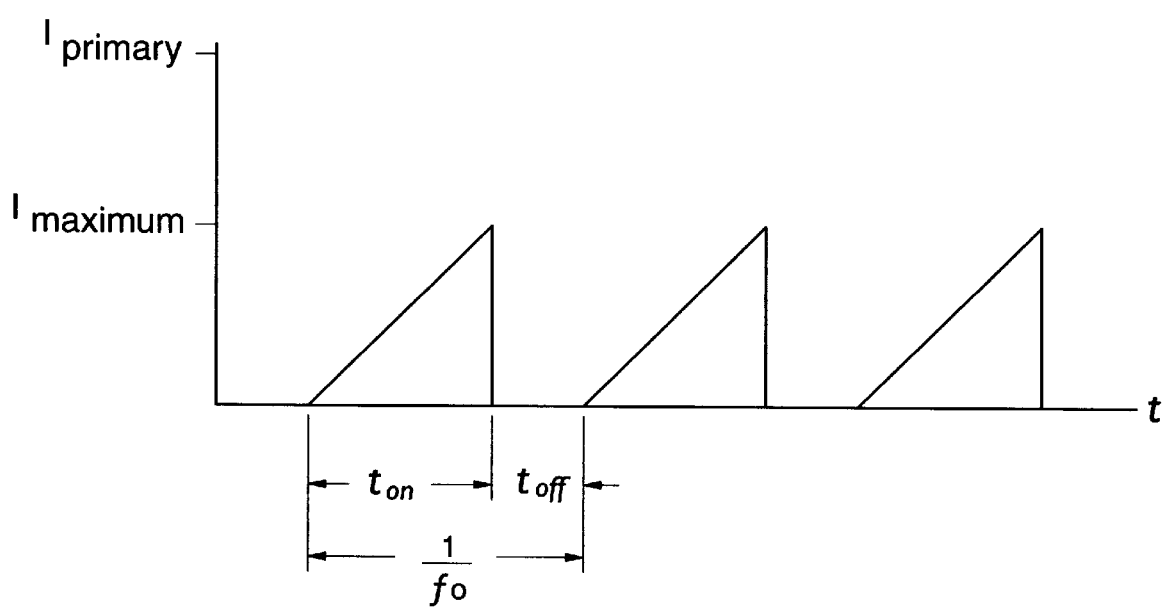
FIG. 3 illustrates a number of charging cycles of a flyback converter.

The voltage drop $V_{load}$ across the sense cell 208 and the sense cell current-sensing resistor 236 is also provided to the A/D 238. The microprocessor 212 calculates the voltage $V_n$ across the sense cell 208 for use in calculations below according to the formula $V_n = V_{load} - V_{sense}$ FIG. 3 illustrates a number of charging cycles of the flyback converter. During an on-time of a charging cycle, the ASIC 210 drives a voltage onto the gate of the flyback FET 214 to close the FET switch and charge the primary winding of the transformer 202. The primary current $I_p$ increases linearly according to the relationship $$\Delta I_p = \frac{\overline{V_p}}{L_p} \Delta t$$

where $L_p$ is the inductance of the primary and $V_p$ is the voltage across the primary. One input of the comparator measures the voltage across the flyback current-sensing resistor $R_p$ 216 to indirectly determine the current flowing through the primary coil. The voltage divider provides a voltage representing the maximum allowable primary current $I_{max}$. When the comparator 218 determines that the sensed current has reached $I_{max}$, it issues a signal to the ASIC 210. In response, the ASIC 210 opens the FET flyback switch 214 to stop charging of the primary. At this point, the on-time ends and the off-time of the charging cycle begins. When the on-time ends, the collapsing field in the primary develops current in the secondary winding, which charges the high-energy capacitor 222.

The present invention recognizes that the energy delivered to the primary during one charging cycle may be represented by the following equation $$E = \tfrac{1}{2} L_p I_{max}^2$$

and that the power delivered during a charging cycle may be represented as $$P = \tfrac{1}{2} f_0 L_p I_{max}^2$$

where T, the period of a charging cycle, is the total of the on-time and the off-time, and $f_0 = 1/T$. The inductance $L_p$, the maximum allowable primary current $I_{max}$, and the desired power P are all known variables. Therefore, solving for $f_0$, $$f_0 = \frac{2P}{L_p I_{max}^2}$$

Based upon this equation, the CPU 212, through the ASIC 210, controls the switching frequency of the flyback FET switch 214 in order to control the power delivered to the primary coil of the transformer 202. The switching frequency is limited by the minimum allowable T that avoids overlap of the on-times of subsequent charging cycles. Based upon limiting $I_p$ to $I_{max}$, $$\min(t_{on}) = \frac{L_p}{V_p} I_{max}$$

The CPU calculates $V_p$ as the battery voltage $V_{batt}$ less $V_{sense}$, the voltage across the flyback current-sensing resistor 216 and the known voltage drop across the flyback FET 214.

Similarly, for the off-time, $$\min(t_{off}) = \frac{L_n}{V_s} I_{max}$$

where the secondary voltage $V_s$ is the capacitor 222 voltage $V_{cap}$ plus secondary voltage losses (nominally 10 volts), and the secondary current $I_{smax}$, is related to the primary current in a well known manner. The highest frequency that the CPU 212 will request is based upon the worst case on and off-times. Note that as the capacitor 222 is charged, $V_s$ increases, and the off-time will decrease, allowing the switching frequency to increase with time.

Figure 4:
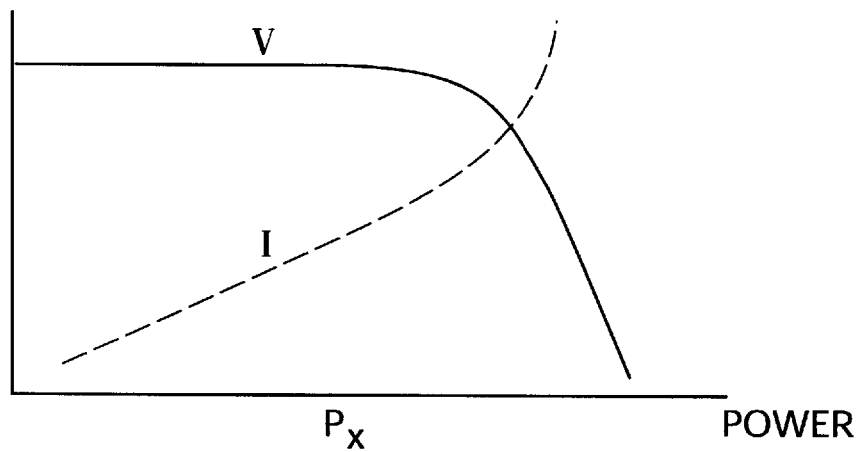
FIG. 4 illustrates voltage and current as a function of the power load on a battery.

FIG. 4 illustrates voltage and current as a function of the power load on a lithium battery. Those skilled in the art will recognize that the present invention is not limited to lithium batteries. Further, for the sake of convenience, the voltage curve will also be referred to as a "capacity curve." The capacity curve exhibits a dramatic drop in voltage when load power exceeds an acceptable maximum power $P_x$. To maintain constant power to the load, the current must conversely increase drastically to offset the decrease in voltage. At some point, the current will increase to a value that will lead to battery failure. Thus, this curve cannot provide an accurate measure of battery capacity because increasing power to take measurements near $P_x$ risks battery failure. Accordingly, conventional battery-operated devices typically limit the load so that the power drawn from the battery lies in the region well below $P_x$, and indicates a low battery well before actual depletion. This mode of operation is acceptable for many applications. However, for some applications, such as cardiac defibrillators, it is preferred to maximize power delivery without causing battery failure. Further, it is generally desired to measure battery capacity more accurately. Accurate measurement permits a low battery warning to be indicated with the assurance that a predetermined battery capacity remains thereafter.

To accomplish these objectives, one embodiment of the present invention adjusts the power load on the battery as a function of the slope of the capacity curve so that it is operating near the knee of the curve of FIG. 4, i.e., at a maximum acceptable power level. The slope of the curve is relatively flat until $P_x$, at which point it begins to turn sharply negative. When the slope falls below a predetermined negative slope threshold value, the CPU, through the ASIC, decreases $f_0$ to lower the power load on the battery so that it is again operating in a safe operating region. One difficulty with this technique is determining the proper slope threshold value. The appropriate slope threshold for a particular battery varies as a function of a number of factors, including capacity, rated voltage and temperature.

Figure 5:
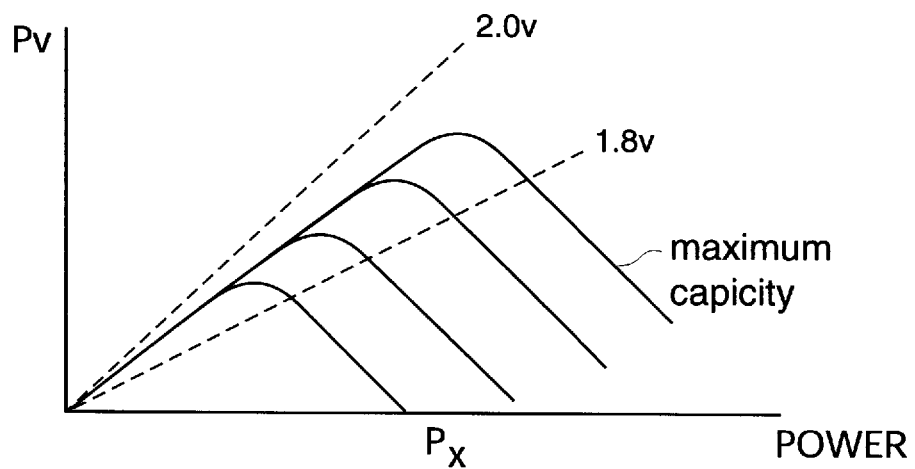
FIG. 5 is a capacity curve plotting the product of power load and battery voltage against power load.

Accordingly, the present invention employs the improved capacity curve of FIG. 5 to overcome this problem. FIG. 5 plots the product of power load and battery voltage against power load. A family of curves is illustrated for different battery capacities. For these curves, the optimum power loading condition occurs at the maximum of each curve. At power levels below the maximum, the slope is essentially the same as the voltage because the voltage is substantially flat below $P_x$. However, for power levels above $P_x$, the voltage falls sharply at a rate faster than the increase in power, thereby causing the product PV to also have a negative slope for power levels above $P_x$. In this embodiment, $P_x$ occurs when the slope is zero, regardless of battery type, capacity, temperature or other environmental conditions. Accordingly, the capacity curve of FIG. 5 is a much more robust measure of optimum power, which is also easier to implement.

The capacity curve of FIG. 5 is preferably employed in a main stack/sense cell arrangement, such as that shown in FIG. 2. The dynamic load controller first optimizes power delivery for the sense cell using a sense cell capacity curve $V_n^2 I_{sense}$ as a function of $V_n I_{sense}$. As the sense becomes depleted and falls below a predetermined capacity, then the dynamic load controller optimizes power delivery based upon a battery capacity curve $V_{batt}^2 I_{batt}$ as a function of $V_{batt} I_{batt}$. Those skilled in the art will recognize that use of the capacity curve of the invention is generally applicable to any battery system.

Figure 6:
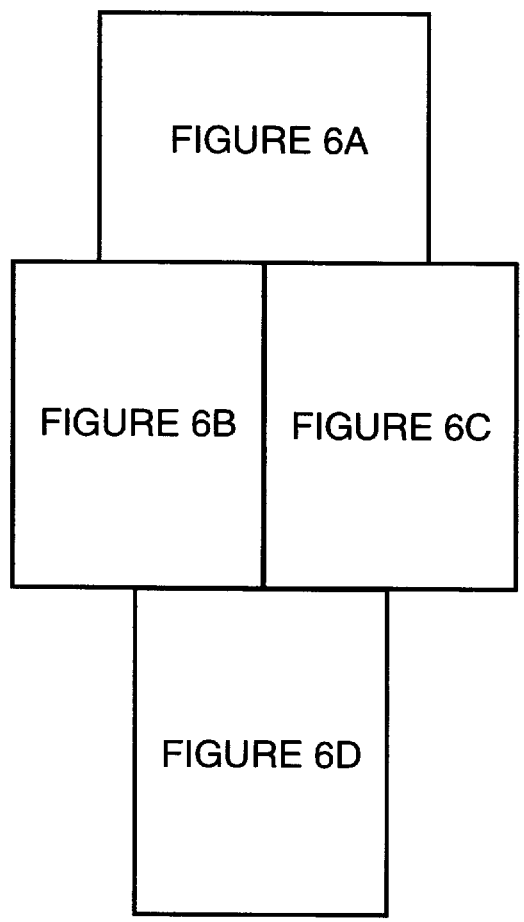
FIG. 6 is a flow chart illustrating the logic of the present invention employed to indicate low battery and depleted battery conditions and to control battery load dynamically in order to optimize power delivery.
Figure 6A:
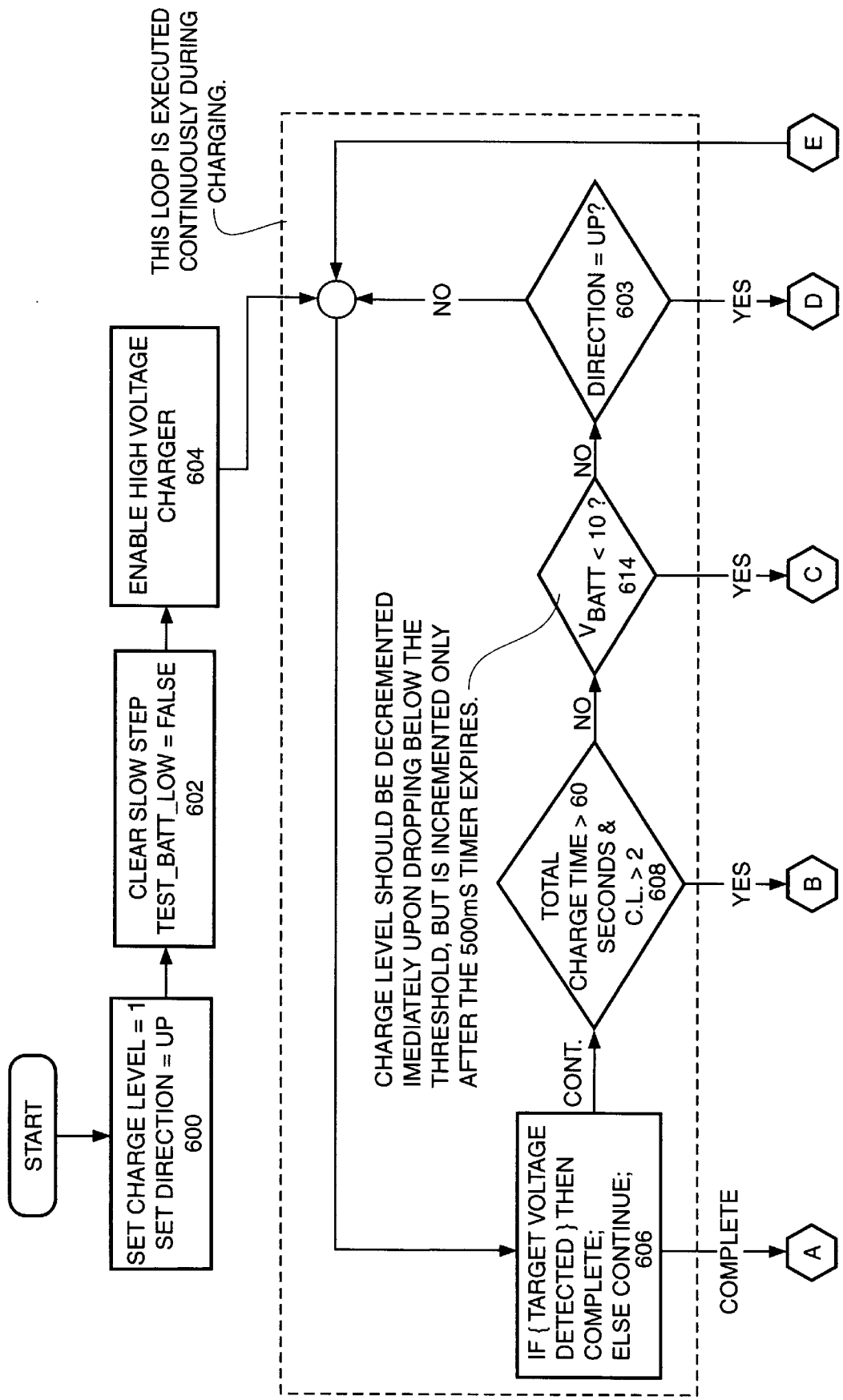
Figure 6B:
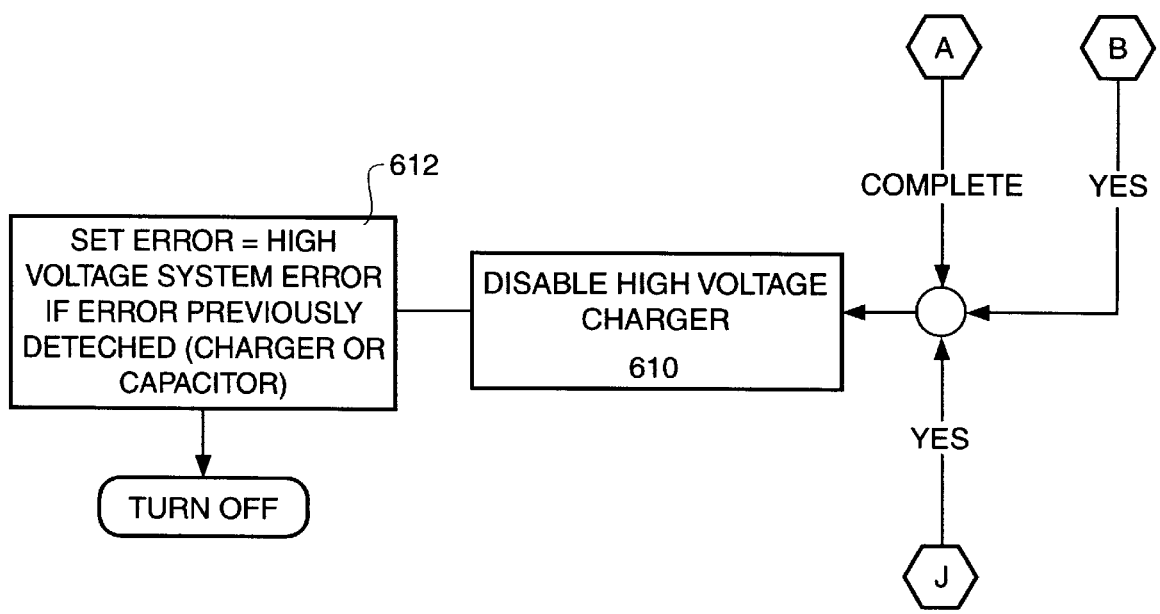
Figure 6C:
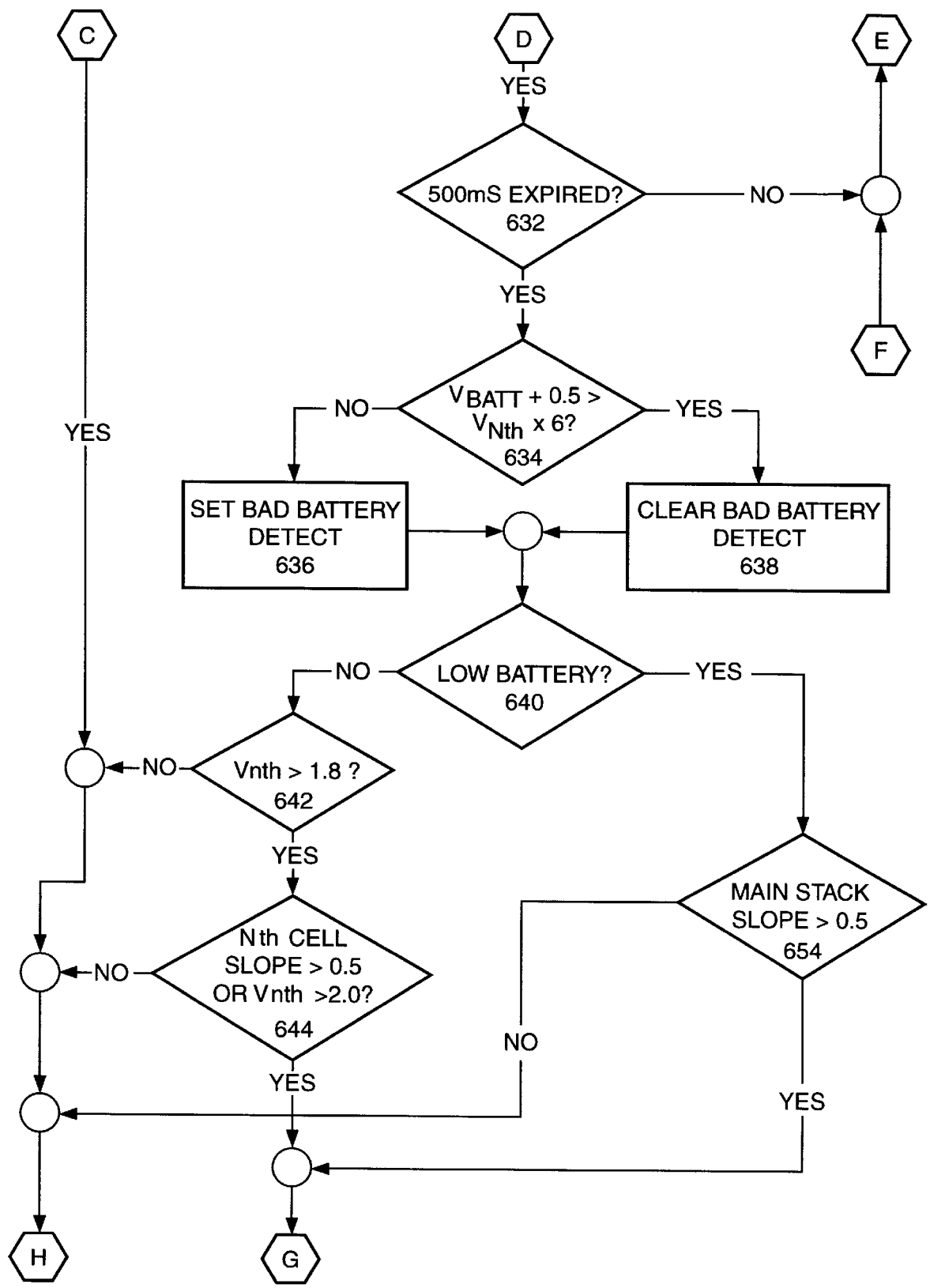
Figure 6D:
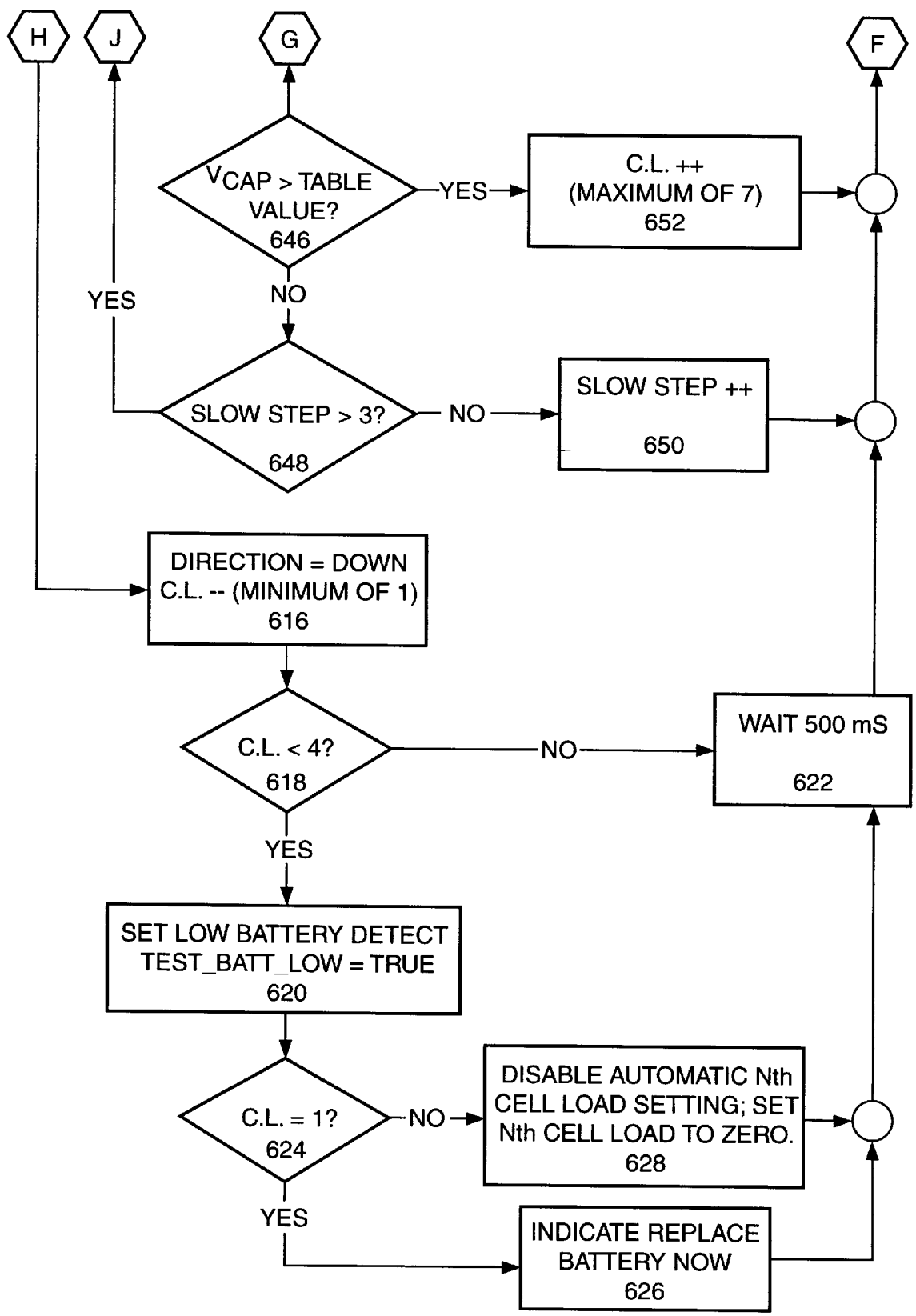

FIG. 6 is a flow diagram illustrating the logic implemented by the CPU and the ASIC to indicate low battery and depleted battery conditions and to control battery load dynamically in order to optimize power delivery in the defibrillator of FIG. 2. The logic initially sets charge level=1 (by adjusting $f_0$) and a direction flag to UP to indicate that charge level is to be increased (step 600). Table 1 illustrates the relationship between charge level and input power to the primary coil of the transformer.

TABLE 1

| CHARGE LEVEL | CHARGER POWER (W) |
|---|---|
| 1 | 5 |
| 2 | 7.5 |
| 3 | 10 |
| 4 | 12.5 |
| 5 | 15 |
| 6 | 17.5 |
| 7 | 20 |

The logic then clears a counter SLOW STEP (step 602) and enables the high-voltage charge of the defibrillator by starting to switch the flyback FET switch 214 at the switching frequency (step 604). The logic then determines whether charging is complete by determining whether the capacitor voltage has reached a target voltage (step 606). If not, then, during charging, the logic determines whether the total charge time exceeds a predetermined time threshold (here, 60 seconds) when the charge level is above a predetermined charge level threshold (here, 2) (step 608). These thresholds are selected so that the system knows that a hardware error has occurred because, at charge levels above the charge level threshold, charging should take less time than the predetermined time threshold. In case of a hardware error, the high-voltage charger is disabled (step 610) and a system error is registered (step 612).

The logic also tests whether the total battery voltage $V_{batt}$ is less than a battery voltage threshold (here, 10 volts) (step 614). If it is, then the logic sets the charge direction flag to the DOWN state, and decrements the charge level (step 616). The logic then determines whether, at this low battery voltage, the battery can maintain power above a predetermined power threshold (step 618). In this example, the logic sets a LOW BATTERY DETECT (test batt low) flag if the charge level is less than 4 (step 620). If, on the other hand, the charge level equals or exceeds the power threshold, then the logic waits a half-second after decrementing the charge level (step 622) to allow the battery voltage to recover for the next test at step 606. The invention allows a "dwell time" (a half-second in this example) for the battery voltage to settle after adjusting power levels before conducting any battery measurements. By allowing the charge level to be decreased, the load controller provides an advantage over prior art fixed-load systems in which the battery is loaded more heavily at lowered capacity than necessary, which leads to a low battery indication when the battery may still be able to deliver effective electrotherapeutic treatment under lighter loading conditions.

In the case that the LOW BATTERY DETECT flag is set, the logic continues to test the charge level to determine whether it is below a minimum power threshold (step 624). In this example, if the charge level is less than 2 (C.L.=1), this indicates that the battery has been depleted, and the logic indicates that battery replacement is necessary (steps 626). If, on the other hand, the minimum power threshold is exceeded, then the logic disables the sense cell loading in order to provide extra capacity to the battery as a whole (step 628). The logic continues at step 622.

Returning to step 614, if, on the other hand, the battery voltage equals or exceeds the battery voltage threshold (10 volts), then the logic determines whether the direction flag is set to UP (step 630). Assuming that charge direction is initially UP, the logic determines whether a half-second has expired since the last time the charge level was adjusted (step 632).

After a half-second has passed, the logic determines whether the total battery voltage is too low based upon a measurement of the sense cell voltage (step 634). In the preferred embodiment, the battery comprises six identical cells including the main stack and the sense cell, otherwise known as the nth cell. If the total battery voltage $V_{batt}$ falls below $6V_n-0.5$ (a small voltage margin), then the logic sets a flag indicating a bad battery (step 636). If not, then the logic clears any bad battery flag that may have been set during a previous charge cycle (step 638). This is one way in which the sense cell helps determine whether the main stack has been depleted.

The logic then determines whether the LOW BATTERY flag has been set (step 640). If not, the logic determines whether the sense cell voltage, $V_n$, is greater than a predetermined low-voltage threshold (step 642). Here, the threshold=1.8 volts. The threshold is selected as the voltage at which the cell has been substantially depleted. If the cell voltage is satisfactory, then the logic determines the slope of the FIG. 5 capacity curve for the sense cell is greater than a predetermined slope threshold or whether the sense cell voltage is greater than a predetermined high-voltage threshold (here 2 volts) (step 644). The sense cell slope, $m_n$, is calculated by the logic as follows:

$$m_n = \frac{V1^2 \times I1 - V2^2 \times I2}{V1 \times I1 - V2 \times I2}$$

where $V1=V_n$, $I1=I_{sense}$ for the current power setting, and $V2=V_n$, $I2=I_{sense}$ for the previous setting.

The predetermined slope threshold is selected to be near zero, i.e., the curve maximum, yet slightly greater than zero to ensure that the load power is not set to a value greater than $P_x$. At power levels greater than $P_x$, the voltage would drop drastically, possibly leading to battery failure. Here, the predetermined slope threshold is preferably selected as 0.5. A slope greater than the slope threshold thus indicates that the charge level need not be decreased in order to avoid battery failure, and that an attempt should be made to increase charge level in order to achieve optimal power delivery. Similarly, a sense cell voltage greater than the high-voltage threshold indicates a healthy sense cell for which an attempt should be made to increase the power load.

Before allowing the charge level to be increased, one embodiment of the present invention first compares the capacitor voltage to the capacitor voltage thresholds shown in Table 2 depending upon the current charge level (step 646).

TABLE 2

| CHARGE LEVEL | VOLTAGE |
|---|---|
| 1 | 117.4 |
| 2 | 186.5 |
| 3 | 258.9 |
| 4 | 310.0 |
| 5 | 360.8 |
| 6 | 444.6 |
| 7 | N/A |

The capacitor voltage thresholds for a particular charge level are calculated to assure that the capacitor voltage is high enough so that the input power to the primary can be incremented by a power increment and still allow sufficient time for the secondary winding to discharge completely into the capacitor before starting the next charging cycle. The values shown in the table correspond to charge level increments of 2.5 watts, as shown in Table 1, a 100 microfarad energy storage capacitor, and a dwell time of a half-second. If the capacitor voltage is not greater than the corresponding capacitor voltage threshold, then the logic increments a counter SLOW STEP to indicate that charging will occur too slowly. If, after a number of dwell time periods (here, a number greater than 3), the defibrillator is still incrementing the SLOW STEP counter, then the logic will disable the high-voltage charger and register a system error (steps 648, 650, 610, 612).

If, on the other hand, the capacitor voltage exceeds the corresponding capacitor voltage threshold, then the charge level is incremented by 1 (step 652), and the logic increases the frequency at which the FET switch is operated to achieve the corresponding power level. The logic continues with step 606.

Returning to steps 642, 644, if these sense cell conditions are negative, then the logic sets the direction flag in the DOWN direction, decrements the charge level (step 616), and performs the steps that follow in the flowchart in a manner similar to the case where the battery voltage fell below the battery voltage threshold.

If the LOW BATTERY DETECT flag is set due to a condition of the sense cell (step 620), then this indicates that the sense cell is nearly depleted, and that power should be optimized with respect to the battery as a whole. Accordingly, the logic determines whether the slope of the capacity curve for the battery exceeds a predetermined battery slope threshold (here, 0.5) (step 654). The battery slope is calculated as $$m_{batt} = \frac{V1^2 \times I1 - V2^2 \times I2}{V1 \times I1 - V2 \times I2}$$

where $V1=V_{batt}$, $I1=I_{batt}$ for the current power setting, and $V2=V_{batt}$, $I2=I_{batt}$ for the previous setting. Note that $I_{batt}=I_{sense}$ at this point because the dummy load has been disabled.

If the battery slope is greater than the slope threshold, then the logic proceeds with step 646, which may result in an increase of charge level. If not, then the logic proceeds to step 616 to decrease the charge level. In this manner, the power level is optimized for the battery with respect to the battery capacity curve. Note that charge level for either the sense cell or the whole battery is never decremented more than once during a dwell time period.

The logic performs this optimization function with respect to the sense cell and the main stack until the logic detects that the voltage on the capacitor has reached a target voltage (step 606). If so, then the charging process is complete, and no more charging cycles are required.

Referring back to the first embodiment of FIG. 4 for determining optimum power level, the flow chart of FIG. 6 may employ the curve of FIG. 4 by substituting a comparison of the FIG. 5 capacity curve slope with a comparison of the FIG. 4 slope to a different slope threshold. That slope threshold would indicate that power cannot be increased when the slope begins to become negative. At that point, the charge level must be decremented.

The invention may be used to provide the ability to deliver a minimum capacity single use when a low battery condition is indicated. The following examples illustrate specific applications of the invention to external defibrillators.

EXAMPLE 1

An external defibrillator was constructed and operated according to the apparatus of FIG. 1 and the logic of FIG. 5, to deliver a 245 Joule truncated exponential biphasic waveform shock. The test was run at 0° C.

A new 80,000 Joule battery was placed in the defibrillator, and the defibrillator was operated to deliver one shock every 15 minutes during ECG monitoring, until the "Low Battery" warning appeared. $I_{sense}$ was controlled to be 20% greater than $I_{batt}$ throughout. Use of the defibrillator then ceased for one hour.

Next, the defibrillator was operated in an end use mode providing groups of three shocks (spaced one minute apart) during a total of five minutes of monitoring. 28,539 Joules were extracted from the battery in the end use mode before the "Low Battery" warning appeared. Thereafter, the battery provided 18,868 Joules until the "Replace Battery" warning appeared. During this final period from "Low Battery" to "Replace Battery," the defibrillator delivered 41 shocks requiring a 60-second charge time (or less). Of these 41 shocks, 32 shocks required less than 30 seconds of charge time.

EXAMPLE 2

This test was performed using an external defibrillator substantially the same as in Example 1 to deliver 245 Joule truncated exponential waveform shocks. The test was run at 25° C.

A new 80,000 Joule battery was placed in the defibrillator, and the defibrillator was operated to deliver one shock every 15 minutes during ECG monitoring, until the "Low Battery" warning appeared. In this example, however, $I_{sense}$ was controlled to be 30% greater than $I_{batt}$ throughout. Use of the defibrillator then ceased for one hour.

Next, the defibrillator was operated in an end use mode providing groups of three shocks (spaced one minute apart) during a total of five minutes of monitoring. 54,451 Joules were extracted from the battery in the end use mode before the "Low Battery" warning appeared. Thereafter, the battery provided 10,573 Joules until the "Replace Battery" warning appeared. During this final period from "Low Battery" to "Replace Battery," the defibrillator delivered 23 shocks requiring a 60-second charge time (or less). Of these 23 shocks, 20 shocks required less than 30 seconds of charge time.

EXAMPLE 3

This test was performed using an external defibrillator substantially the same as in Example 1 to deliver 245 Joule truncated exponential waveform shocks. The test was run at 25° C.

A new 80,000 Joule battery was placed in the defibrillator, and the defibrillator was operated to deliver shocks in groups of fifteen (with no monitoring), followed by 30 minutes of inactivity, until the "Low Battery" warning appeared. $I_{sense}$ was controlled to be 20% greater than $I_{batt}$ throughout. Use of the defibrillator then ceased for one hour.

Next, the defibrillator was operated in an end use mode providing groups of three shocks (spaced one minute apart) during a total of five minutes of monitoring. 47,809 Joules were extracted from the battery in the end use mode before the "Low Battery" warning appeared. Thereafter, the battery provided 7371 Joules until the "Replace Battery" warning appeared. During this final period from "Low Battery" to "Replace Battery," the defibrillator delivered 16 shocks requiring a 60-second charge time (or less). Of these 16 shocks, 13 shocks required less than 30 seconds of charge time.

EXAMPLE 4

This test was performed using an external defibrillator substantially the same as in Example 1 to deliver 245 Joule truncated exponential waveform shocks. The test was run at 0° C.

A new 80,000 Joule battery was placed in the defibrillator, and the defibrillator was operated to deliver shocks in groups of fifteen (with no monitoring), followed by 30 minutes of inactivity, until the "Low Battery" warning appeared. $I_{sense}$ was controlled to be 30% greater than $I_{batt}$ throughout. Use of the defibrillator then ceased for one hour.

Next, the defibrillator was operated in an end use mode providing groups of three shocks (spaced one minute apart) during a total of five minutes of monitoring. 20,355 Joules were extracted from the battery in the end use mode before the "Low Battery" warning appeared. Thereafter, the battery provided 20,213 Joules until the "Replace Battery" warning appeared. During this final period from "Low Battery" to "Replace Battery," the defibrillator delivered 44 shocks requiring a 60-second charge time (or less). Of these 44 shocks, 38 shocks required less than 30 seconds of charge time.

All references cited herein are incorporated by reference herein in their entirety. Further, it will be appreciated that various modifications and alterations might be made by those skilled in the art without departing from the spirit and scope of the present invention. The invention should, therefore, be measured in terms of the claims which follow.

What is claimed is:

1. In an electrotherapy device including a power source for delivering power to a flyback transformer for charging an energy storage capacitor at a plurality of charge levels, a charge control circuit for optimizing delivery of said power, said charge control circuit coupled to said power source to select said charge level and to said energy storage capacitor for measuring a voltage across said energy storage capacitor, wherein said charge control circuit compares said voltage to one of a plurality of capacitor voltage thresholds according to said charge level and, if said voltage exceeds said one of said plurality of capacitor thresholds, incrementing said charge level.

2. The charge control circuit according to claim 1 wherein if said voltage does not exceed said one of said plurality of capacitor thresholds, disabling said power source after a predetermined number of dwell time periods.

3. In an electrotherapy device including a power source for delivering power to a flyback transformer for charging an energy storage capacitor at a plurality of charge levels, a method for optimizing delivery of said power comprising:

selecting one of said charge levels;

measuring a voltage across said energy storage capacitor;

comparing said voltage to one of a plurality of capacitor voltage thresholds according to said one charge level; and if said voltage exceeds said one of said plurality of capacitor thresholds, incrementing said charge level.

4. The method for optimizing delivery of said power according to claim 3 further comprising:

if said voltage does not exceed said one of said plurality of capacitor thresholds, disabling said power source after a predetermined number of dwell time periods.

* * * * *

UNITED STATES PATENT AND TRADEMARK OFFICE
CERTIFICATE OF CORRECTION

PATENT NO. : 5,889,388                                    Page 1 of 2
DATED      : March 30, 1999
INVENTOR(S) : Cameron et al.

It is certified that error appears in the above-identified patent and that said Letters Patent is hereby corrected as shown below:

Column 3, (line 24), after "threshold." begin a new paragraph.

Column 7, (line 3), delete "$f_0\_1/T$" and insert therefor --$f_0=1/T$--.

Column 7, (line 28), delete "$\min(t_{off}) = \frac{L_n}{V_s} I_{max}$" and insert therefor $$-- \min(t_{off}) = \frac{L_s}{V_s} I_{s\,max} --.$$

Column 7, (line 32), after "$I_{s\,max}$" delete ",".

Column 8, (line 29), after "sense" insert --cell--.

UNITED STATES PATENT AND TRADEMARK OFFICE
CERTIFICATE OF CORRECTION

PATENT NO. : 5,889,388
DATED : Mar. 30, 1999
INVENTOR(S) : Cameron, et al

It is certified that error appears in the above-indentified patent and that said Letters Patent is hereby corrected as shown below:

Column 9, line 64, after "determines" insert —whether—

Signed and Sealed this

Second Day of November, 1999

Attest:

Attesting Officer

Q. TODD DICKINSON

Acting Commissioner of Patents and Trademarks